(12) United States Patent
Coelho (10) Patent No.: US 11,839,905 B2
(45) Date of Patent: Dec. 12, 2023

(54) VIBRATING BASE ASSEMBLY FOR CLEANING CONTACT LENSES

(71) Applicant: Ekhoo, LLC, Austin, TX (US)

(72) Inventor: Alexandre Coelho, Austin, TX (US)

(73) Assignee: EKHOO, LLC, Austin, TX (US)

( * ) Notice: Subject to any disclaimer, the term of this patent is extended or adjusted under 35 U.S.C. 154(b) by 0 days.

(21) Appl. No.: 17/519,300

(22) Filed: Nov. 4, 2021

(65) Prior Publication Data

US 2023/0136056 A1    May 4, 2023

(51) Int. Cl.
| | |
|---|---|
| *B08B 3/04* | (2006.01) |
| *G02C 13/00* | (2006.01) |
| *A61L 12/02* | (2006.01) |

(52) U.S. Cl.
CPC ............ *B08B 3/044* (2013.01); *A61L 12/026* (2013.01); *G02C 13/008* (2013.01)

(58) Field of Classification Search
CPC ..... G02C 13/00; G02C 13/008; A61L 12/026; B08B 3/044; B08B 3/12
See application file for complete search history.

(56) References Cited

U.S. PATENT DOCUMENTS

| | | | |
|---|---|---|---|
| 3,113,761 A * | 12/1963 | Platzman | ............... B08B 3/12 |
| | | | 366/115 |
| 3,139,097 A | 6/1964 | Hungerford et al. | |
| 3,614,959 A | 10/1971 | Schollmaier et al. | |
| 4,597,399 A | 7/1986 | Rabenau et al. | |
| 4,691,725 A | 9/1987 | Parisi | |

(Continued)

FOREIGN PATENT DOCUMENTS

| | | |
|---|---|---|
| CH | 561053 A5 * | 4/1975 |
| EP | 0178756 A1 | 4/1986 |

(Continued)

OTHER PUBLICATIONS

Machine translation of JP-2013011876-A, dated Jan. 2013. (Year: 2013).*

(Continued)

*Primary Examiner* — Michael E Barr
*Assistant Examiner* — Kevin G Lee
(74) *Attorney, Agent, or Firm* — Mark C. Johnson; Johnson Dalal (57) ABSTRACT

An integrated and standalone vibrating base assembly for cleaning contact lenses having two selective modes of operation, each mode operably configured to produce different preset vibrational rotations per minute, and comprising a base housing defining a housing cavity, with at least one vibration motor disposed within the housing cavity, electrically coupled to a power source, and operably configured to selectively induce a vibration therefrom with at least one switch coupled to the base housing; and a bottom surface and an upper surface spanning inwardly toward the housing cavity from an upper edge of the base housing to define a concave recess sized to receive two contact lens containers, the upper surface of a friction-inducing, deformable, and polymeric material configured to support two contact lens containers and operably coupled to the at least one vibration motor and to receive a vibration thereon upon activation of the at least one switch.

16 Claims, 7 Drawing Sheets

(56) References Cited

U.S. PATENT DOCUMENTS

| | | | |
|---|---|---|---|
| 4,957,128 A * | 9/1990 | Chen | G02C 13/008 |
| | | | 134/140 |
| 4,965,904 A | 10/1990 | Tanaka et al. | |
| 5,129,410 A | 7/1992 | Ifejika | |
| 6,080,361 A | 6/2000 | Borovsky | |
| 6,193,806 B1 * | 2/2001 | Reed | A45C 11/005 |
| | | | 134/1 |
| 8,015,987 B2 | 9/2011 | Zakutin | |
| 8,211,237 B2 | 7/2012 | Simonette | |
| 10,328,644 B2 | 6/2019 | Filippo | |
| 2004/0182428 A1 | 9/2004 | Chepurny | |
| 2008/0031094 A1 * | 2/2008 | Laugharn | C01B 25/327 |
| | | | 367/138 |
| 2009/0283118 A1 * | 11/2009 | Zakutin | A61L 12/02 |
| | | | 134/184 |
| 2014/0318573 A1 * | 10/2014 | Cheon | B08B 3/12 |
| | | | 134/1 |
| 2016/0279680 A1 * | 9/2016 | Lutz | B08B 3/12 |
| 2020/0333637 A1 * | 10/2020 | Greeson | G02C 13/008 |
| 2021/0286199 A1 * | 9/2021 | Sun | G02C 13/008 |

FOREIGN PATENT DOCUMENTS

| | | | |
|---|---|---|---|
| JP | 2013011876 A | * | 1/2013 |
| KR | 19980087837 A | * | 12/1998 |
| KR | 2001107370 A | * | 12/2001 |
| WO | 8900429 | | 1/1989 |
| WO | 2018223792 A1 | | 12/2019 |

OTHER PUBLICATIONS

Machine translation of KR-2001107370-A, dated Dec. 2001. (Year: 2001).*

Machine translation of KR-19980087837-A, dated Dec. 1998. (Year: 1998).*

* cited by examiner

FIG. 7

VIBRATING BASE ASSEMBLY FOR CLEANING CONTACT LENSES

FIELD OF THE INVENTION

The present invention relates generally to assemblies operably configured to clean contact lenses and, more particularly, relates to structures operably configured to retain and vibrate containers housing one or more contact lenses.

BACKGROUND OF THE INVENTION

Contact lenses provide the comfort and convenience of improved eyesight without the hassle involved in wearing eyeglasses. However, proper lens hygiene is paramount and special care must be taken in cleaning and disinfecting contact lenses after every use to prevent the development of vision-related medical issues from arising, e.g., eye infection, blurred or fuzzy vision, red or irritated eyes, uncomfortable lenses, and pain in or around the eyes. An effective cleaning process is vital to ensure comfortable and infection-free contact lens wear, allowing for better eye health and vision. A proper disinfection cycle involves using a multi-purpose solution with soft contact lenses and rubbing the contact lens for between 2 and 20 seconds, depending on the contact lens care solution. This practice removes protein and residue build-up (surface deposits) and micro-organisms and reduces complications, promoting cleaner lenses. Some recent evidence conclusively demonstrates that rubbing and rinsing lens after wear provides the safest lens wear for all contact lenses and care systems currently on the market. The rubbing of lenses is typically done with a user's fingertips which may sometimes cause damage to contact lenses. As such, existing prior art discloses vibrating devices operably configured to clean and disinfect contact lenses. See, e.g., Schollmaier et al. (Alcon Laboratories Inc.), U.S. Pat. No. 3,614,959 A (Oct. 26, 1971); David Michael Zakutin, U.S. Pat. No. 8,015,987 B2 (Sep. 13, 2011); Tanaka et al. (Menicon Co Ltd.), U.S. Pat. No. 4,965,904 A (Oct. 30, 1990); Mark Chepurny, U.S. Patent Publication No. 2004/0182428A1 (Sep. 23, 2004); Rebecca A. Simonette, U.S. Pat. No. 8,211,237 B2 (Jul. 3, 2012).

However, the existing prior art is characterized by significant drawbacks including, without limitation, the excessive noise caused by the vibrating mechanism which can be inconvenient, bothersome, and aggravating to a user, as well as the inability to designate and set different cleaning modes to facilitate various cleaning needs. Additionally, known prior art often entails the use of components that may be bulky and require assembly or external components, e.g., requiring assembly, connectors, external power source, etc. Some prior art fails to adequately clean, sanitize, and disinfect contact lens and, in fact, has the opposite effect, because it is designed in a way whereby the contact lenses must be directly placed within the cleaning device, exposing the lenses to dirt, dust, rust, germs, residue from prior uses, and other foreign particles resident on the cleaning device.

Therefore, a need exists to overcome the problems with the prior art as discussed above.

SUMMARY OF THE INVENTION

The invention provides an integrated and standalone vibrating base assembly for cleaning contact lenses that overcomes the hereinafore-mentioned disadvantages of the heretofore-known devices and methods of this general type and that provides a simple and easy way to gently clean contact lenses and promote healthy eyes. Embodiments of the invention reduce protein and residue build-up that may cause eye infections and other serious or bothersome eye concerns. Routine use of the present invention is also recommended as part of a hygienic routine to reduce damage caused by the excessive use of rubbing fingertips when cleaning lenses.

With the foregoing and other objects in view, there is provided, in accordance with the invention, a vibrating base assembly for cleaning contact lenses comprising a base housing defining a housing cavity, with an upper edge, with at least one vibration motor disposed within the housing cavity, electrically coupled to a power source, and operably configured to selectively induce a vibration therefrom with at least one switch coupled to the base housing; and a bottom surface and an upper surface opposing the bottom surface of the vibrating base assembly and spanning inwardly toward the housing cavity from the upper edge of the base housing to define a concave recess relative to the upper edge of the base housing and sized to receive two contact lens containers the upper surface of a friction-inducing, deformable, and polymeric material configured to support two contact lens containers and operably coupled to the at least one vibration motor and receive a vibration thereon upon activation of the at least one switch.

In accordance with another feature, an embodiment of the present invention includes at least one support pad of a friction-inducing material and at least partially defining the bottom surface of the vibrating base assembly.

In accordance with a further feature of the present invention, the vibrating base assembly further comprises an upper support wall of a polymeric material, defining at least a portion of the upper surface defining the concave recess, with a bottom wall portion defining a portion of the upper surface and defining a lens support plane parallel and non co-planar with a base support plane defined by the bottom surface, and with a sidewall portion spanning inwardly toward the housing cavity from the upper edge of the base housing and surrounding the bottom wall portion.

In accordance with a further feature of the present invention, the vibrating base assembly also includes an internal support member retaining the at least one vibration motor, wherein the at least one vibration motor is adjacent and below the bottom wall portion.

In accordance with the present invention, the sidewall portion includes at least one arcuate portion defining, with an opposing surface of the sidewall portion, a central width, and defining two defined circular portions partially defined with the at least one arcuate portion interposed thereon, the two defined circular portions configured to support two contact lens containers.

In accordance with another feature, an embodiment of the present invention also includes two vibration motors with one of the two vibration motors disposed adjacent and below the bottom wall portion of each of the two defined circular portions.

In accordance with yet another feature, an embodiment of the present invention includes a first side retention member protruding from the sidewall portion on one of the two defined circular portions and of the friction-inducing, deformable, and polymeric material; and a second side retention member opposing the first side retention member protruding from the sidewall portion on another of the two defined circular portions and of the friction-inducing, deformable, and polymeric material.

In accordance with a further feature of the present invention, the vibrating base assembly includes at least one floor retention member protruding from the bottom wall portion on and centrally disposed on one of the two defined circular portions, partially surrounded by the first side retention member, and of the friction-inducing, deformable, and polymeric material; and at least one floor retention member protruding from the bottom wall portion on and centrally disposed on another of the two defined circular portions, partially surrounded by the second side retention member, and of the friction-inducing, deformable, and polymeric material.

In accordance with another feature, the base housing further comprises a housing ledge recessed from the upper edge and with the upper support wall selectively removably coupled thereto, the upper support wall of a monolithic structure.

In accordance with yet another feature, an embodiment of the present invention further comprises an electronic controller electrically coupled to the power source and communicatively coupled to the at least one vibration motor; and at least two switches translatably coupled to the base housing, wherein one of the at least two switches is operably configured to induce the vibration from the at least one vibration motor in a first mode with a constant vibration for a first mode period of time and a first mode vibrational rotations per minute and another of the at least two switches is operably configured to induce the vibration from the at least one vibration motor in a second mode with a cyclic constant vibration for a second mode period of time and a second mode vibrational rotations per minute, wherein the first mode vibrational rotations per minute is less than the second mode vibrational rotations per minute.

In combination with a pair of contact lens containers having a lens base and a lens cap selectively removably coupled to the lens base, the present invention comprises a vibrating base assembly with a base housing defining a housing cavity, with an upper edge, with at least one vibration motor disposed within the housing cavity, electrically coupled to a power source, and operably configured to selectively induce a vibration therefrom with at least one switch coupled to the base housing; a bottom surface and an upper surface opposing the bottom surface of the vibrating base assembly; and an upper support wall of a friction-inducing, deformable, and polymeric material, defining at least a portion of the upper surface, with a bottom wall portion, and with a sidewall portion surrounding the bottom wall portion and spanning inwardly toward the housing cavity from the upper edge of the base housing to define a concave recess relative to the upper edge of the base housing and with the lens base of the pair of contact lens containers disposed therein and supported with the upper support wall, the upper support wall operably coupled to the at least one vibration motor and to receive a vibration thereon upon activation of the at least one switch.

In accordance with a feature of the improvement, the bottom wall portion defines a portion of the upper surface and defines a lens support plane parallel and non co-planar with a base support plane defined by the bottom surface.

In accordance with another feature of the present improvement, the present invention also includes at least one support pad of a friction-inducing, deformable, and polymeric material and at least partially defining the bottom surface of the vibrating base assembly.

In accordance with a further feature of the present improvement, an embodiment of the present improvement further includes an internal support member retaining the at least one vibration motor.

In accordance with yet another feature of the present improvement, the sidewall portion includes at least one arcuate portion defining, with an opposing surface of the sidewall portion, a central width, and defining two defined circular portions partially defined with the at least one arcuate portion interposed thereon, the two defined circular portions configured to support at least one contact lens container.

In accordance with a feature of the present improvement, the vibrating base assembly comprises at least one of a first side retention member protruding from the sidewall portion and of the friction-inducing, deformable, and polymeric material; a second side retention member opposing the first side retention member protruding from the sidewall portion and of the friction-inducing, deformable, and polymeric material; a floor retention member protruding from the bottom wall portion and of the friction-inducing, deformable, and polymeric material; or a floor retention member protruding from the bottom wall portion and of the friction-inducing, deformable, and polymeric material.

In accordance with another feature, the present improvement further comprises an electronic controller electrically coupled to the power source and communicatively coupled to the at least one vibration motor; and at least one switch translatably coupled to the base housing, wherein the at least one switch is operably configured to induce the vibration from the at least one vibration motor in a first mode with a constant vibration for a first mode period of time and a first mode vibrational rotations per minute.

In accordance with a further feature, the at least one switch is operably configured to induce the vibration from the at least one vibration motor in a second mode with a cyclic constant vibration for a second mode period of time and a second mode vibrational rotations per minute.

Although the invention is illustrated and described herein as embodied in a vibrating base assembly, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the base housing, from one left end side to a right end side opposing the left end side. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient hygienic device that uses proprietary sonic technology to aid in the cleansing and prevention of surface deposits on contact lenses (e.g., soft hydrogel, silicone hydrogel, hybrid, hard/RGP, colored, etc.). Embodiments of the invention provide a vibrating base assembly that is operably configured to be used in combination with contact lens cases as part of lens wearers' hygienic routine to beneficially reduce damage caused by the excessive use of rubbing fingertips when cleaning contact lenses. In addition, embodiments of the invention provide two different cleaning modes for selection by a user, namely, a "sleep" mode and a "fast" mode, which can be selectively activated based on the needs and preferences of the user. As used herein, the terms "sleep" mode and "fast" mode are meant only to identify the varying modes and are not to be construed as limiting in any way. Embodiments of the present invention also provide an assembly that can operate without the generation or output of excessive noise, i.e., an assembly that operates quietly, and that can operate without the need for additional external components, e.g., assemblies, connectors, external power sources, etc. The present invention is operably configured to come into direct contact with the contact lens case or container, not the contact lenses themselves as is the case with some prior art, which prevents the lenses from being exposed to dirt, dust, rust, germs, and other foreign particles that may be resident on the assembly itself.

Figure 1:
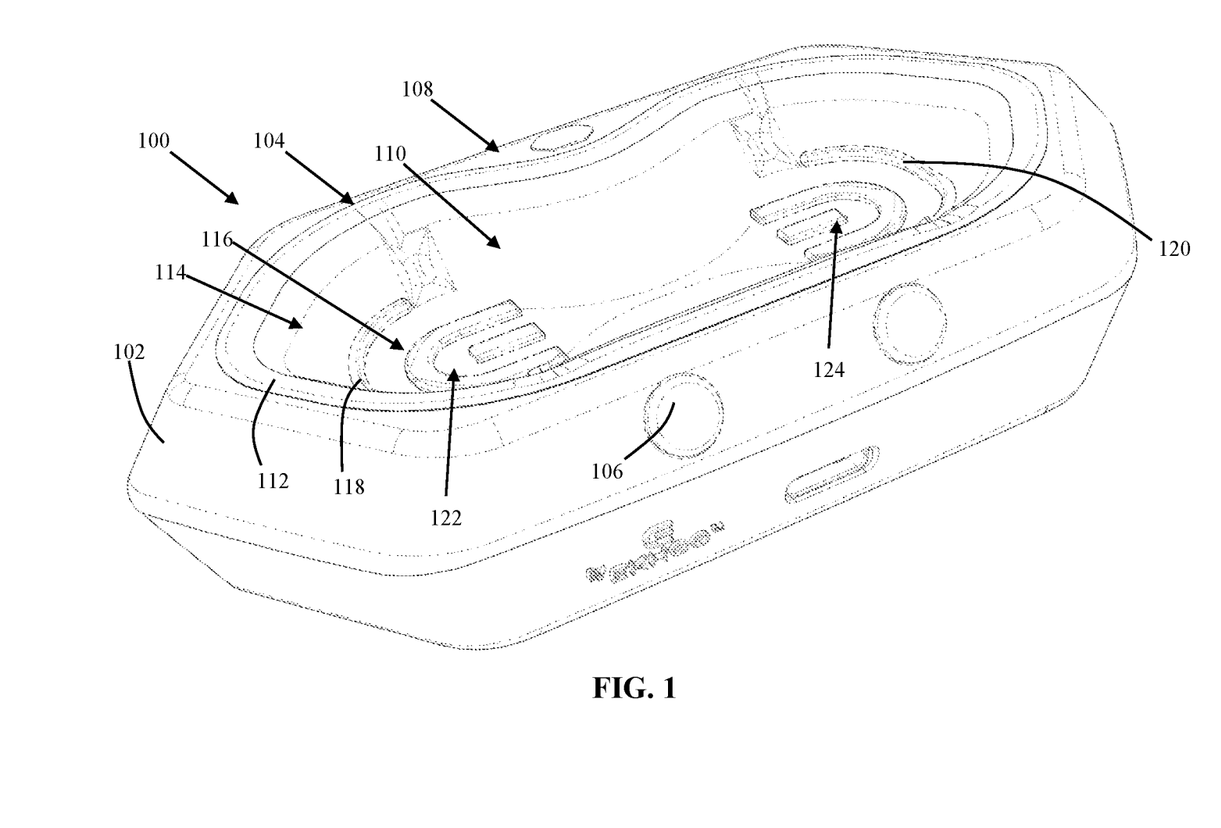
FIG. 1 is a perspective front view of a vibrating base assembly, in accordance with an exemplary embodiment of the present invention.

Referring now to FIG. 1, one embodiment of the present invention is shown in a perspective front view. FIG. 1 shows several advantageous features of the present invention, but, as will be described below, the invention can be provided in several shapes, sizes, combinations of features and components, and varying numbers and functions of the components. The first example of a vibrating base assembly 100 (hereinafter referred to as "assembly 100" for brevity), as shown in FIG. 1, includes a base housing 102 defining a housing cavity 300, with an upper edge 108, with or more one vibration motor(s) 302, 304 disposed within the housing cavity 300. The base housing 102 is preferably of a thermoplastic polyurethane (TPU) silicone or high-density polyethylene (HDPE) composition, having several beneficial properties including, without limitation, high abrasion resistance, high shear strength, and oil and grease resistance. In alternate embodiments, the base housing 102 may be of an alternate material composition having similar properties.

Figure 3:
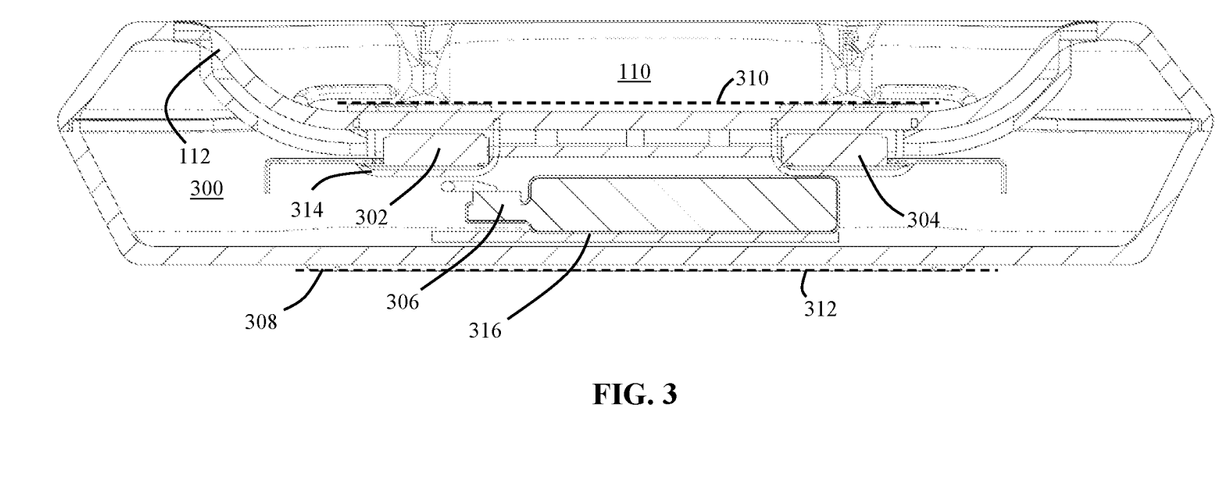
FIG. 3 is a cross-sectional front view across the section line reflected in FIG. 2 of the vibrating base assembly, in accordance with the present invention.

The base housing 102 comprises the at least one vibration motor 302, 304 (i.e., one or more than one) and, in an exemplary embodiment, comprises two (2) Eccentric Rotating Mass vibration motors (ERMs). Exemplary vibration motors 302, 304 consist of 2 3 VDC motors producing between 1200 and 1600 revolutions per minute (RPM), a voltage of approximately 1-1.5V, having wire leads and an operating temperature of approximately –20° C.~70° C., and being used for vibration alerting and haptic feedback. The vibration motors 302, 304 are suitable for single/double cell power buses of Alkaline, Zinc, Silver Oxide and single cell Lithium primary sources, NiCd, NiMH, and Li-ion secondary rechargeable batteries. The at least one vibration motor 302, 304 is electrically coupled to a power source 306, and operably configured to selectively induce a vibration therefrom with at least one switch 106 coupled to the base housing 102. In one embodiment, the base housing 102 is formed with two shell members operably configured to couple together around a perimeter edge or surface thereon to form the housing cavity 300 and one or more enclosed aperture(s) for the switch(es) 106 and an enclosed aperture for an upper support wall 112.

Beneficially, the vibration motors 302, 304 overcome the known limitations of the heretofore-known devices and methods of this general type by operating in a much quieter fashion that is not excessively disturbing or bothersome to those in close proximity to the assembly 100. In one embodiment, the power source 306 is a USB-C charging port (seen in FIG. 3) operably configured to selectively recharge a main lithium-ion battery (which may also be considered a power source 306) housed within the base housing 102. The power source 306 beneficially allows the assembly 100 to be recharged without the need for bulky or inconvenient external or ancillary component such as connectors, wires, cables, etc. The power source 306 may comprise, or function in conjunction with, a printed circuit board (PCB) consisting of a laminated structure of conductive and insulating layers. Due to the compact and rechargeable characteristics of the power source 306, the assembly 100 beneficially lacks the need for any additional or external components, parts, connectors, or support structures and requires no user assembly, i.e., it is preassembled. The switch 106 may include a button covering the switch 106 or otherwise operably coupled thereto for manipulation by a user. The operation and operation mode (as further described hereinafter) of the assembly 100 is designed to be selectively manipulated by the user using the switch 106. In a preferred embodiment, the switch 106 is of a thermoplastic rubber (TPR) composition for greater ease of manipulation and may vary in alternate embodiments. The base housing is approximately between 5 to 6 centimeters wide, 10 to 11 centimeters long, and 2 to 3 centimeters high in a preferred embodiment, to provide a compact and portable size, dimension, and configuration of the assembly 100.

It should be understood that terms such as, "front," "rear," "side," top," "bottom," and the like are indicated from the reference point of a viewer viewing the base housing 102 from the front thereof (see FIG. 1).

Figure 5:
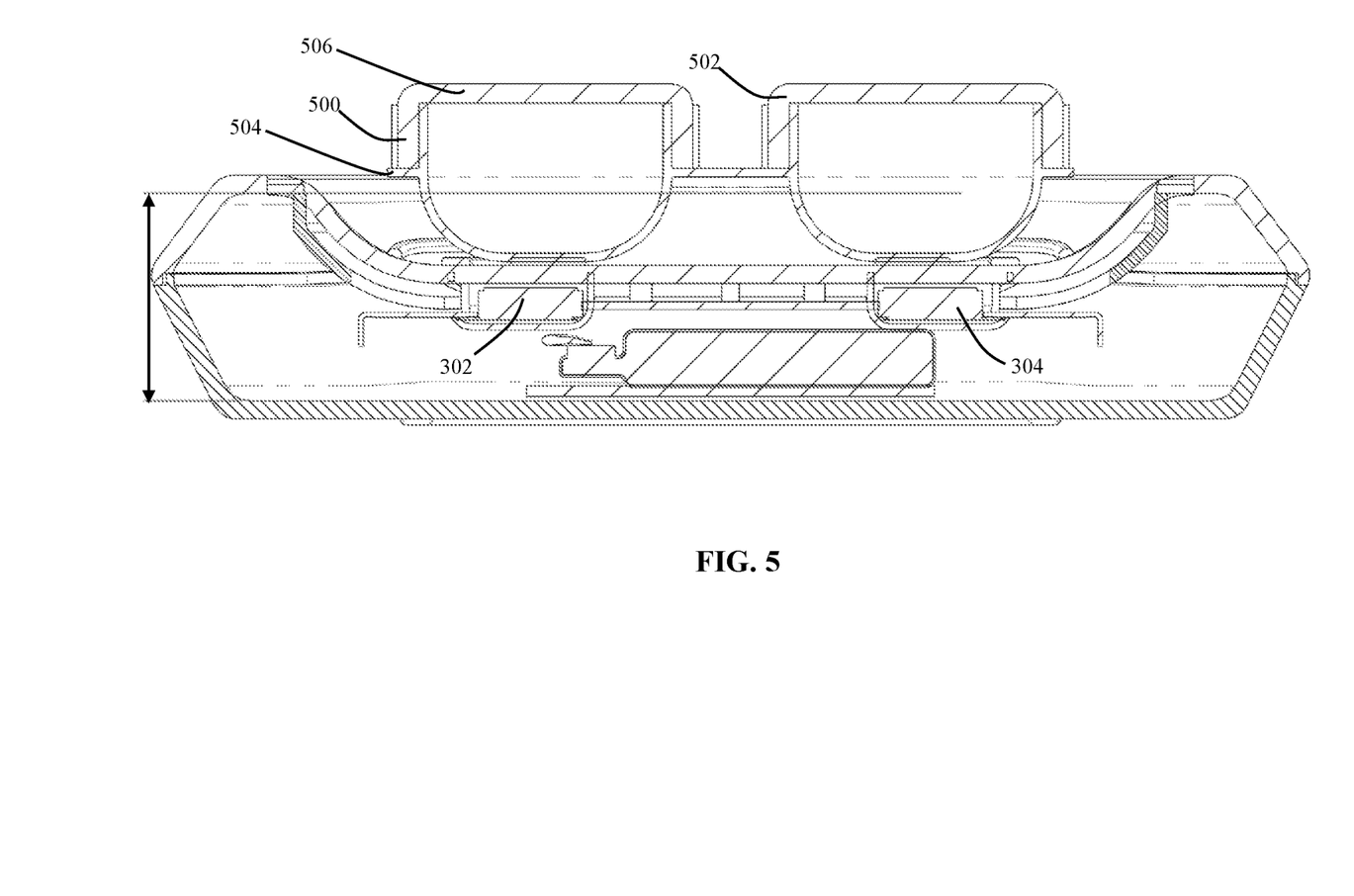
FIG. 5 is a cross-sectional front view across the section line reflected in FIG. 4 of the vibrating base assembly in combination with a pair of contact lens containers, in accordance with the present invention.
Figure 7:
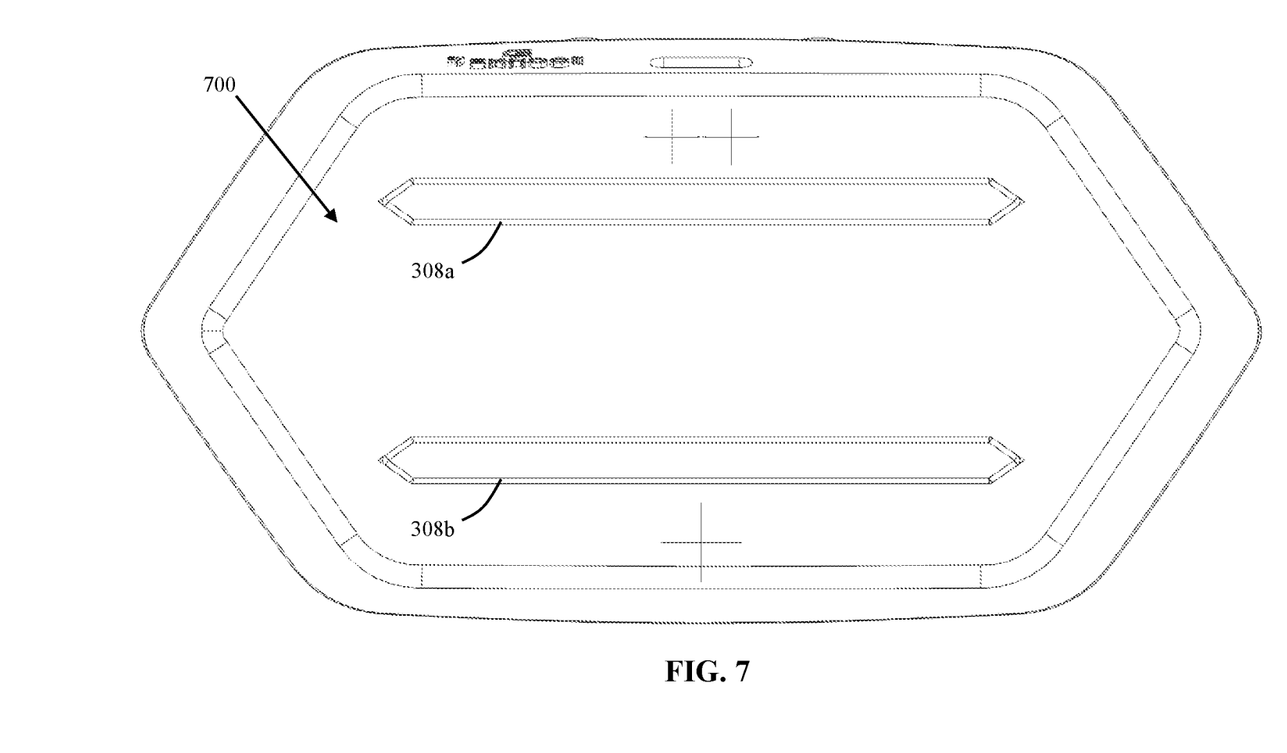
FIG. 7 is a bottom plan view of the vibrating base assembly, in accordance with the present invention.

The assembly 100 also includes a bottom surface 700 (as best depicted in FIG. 7) and an upper surface 104 that can be seen opposing the bottom surface 700 and seen spanning inwardly toward the housing cavity 300 from the upper edge 108 of the base housing 102 to define a concave recess 110 relative to the upper edge 108 of the base housing 102 and sized to receive two contact lens containers 500, 502. The two contact lens containers 500, 502 may be any generally available containers 500, 502 known in the industry such that the assembly facilitates a universal or one-size-fits-most application to most lens cases or containers. Exemplary dimensions of the two contact lens containers 500, 502 are approximately 2.3 inches to 3.4 inches in length, approximately 1 inch to 2 inches in width, and approximately 0.5 inches to 1 inches in height. As such, the concave recess 110 of the base housing 102 is proportionately sized and shaped to receive two contact lens containers 500, 502.

The assembly 100 may further comprise at least one support pad 308 (depicted in FIG. 3 and FIG. 7) of a friction-inducing material and at least partially defining the bottom surface 700 of the vibrating base assembly 100. In a preferred embodiment, the assembly 100 comprises two support pads 308a, 308b (best depicted in FIG. 7) longitudinally disposed on the bottom surface 700 of the assembly 100. The support pad 308 is operably configured to produce friction between the bottom surface 700 of the assembly 100 and the solid surface on which the assembly 100 rests, e.g., bathroom counter, table, drawer, etc., in order to control or stop forward or backward motion of the assembly 100, i.e., to prevent the assembly 100 from inadvertently or accidentally slipping, sliding, or falling. The friction-inducing material of the support pad 308 may include organic and non-organic substances such as resin, ceramics, fibers, and metals. In an exemplary embodiment, the friction-inducing material is a thermoplastic rubber (TPR), natural rubber, chloroprene, polysiloxane, nitrile butadiene rubber (NBR), ethylene propylene diene monomer (EPDM), styrene-butadiene rubber (SBR), isobutylene isoprene, fluorosilicone rubber, or another elastomer having a high coefficient of friction with respect to other contact materials (friction coefficient ranging between 1.0 and 4.0). Because many friction-inducing materials have a limited lifespan, it may be necessary to closely monitor and replace the support pad 308 when it no longer exhibits the beneficial friction-inducing properties or characteristics. The support pad 308 preferably spans longitudinally across at least 50% of the length of the bottom surface 700 of the assembly 100 so as to provide a greater level of friction and slip resistance between the assembly 100 and the solid surface upon which it rests.

Figure 2:
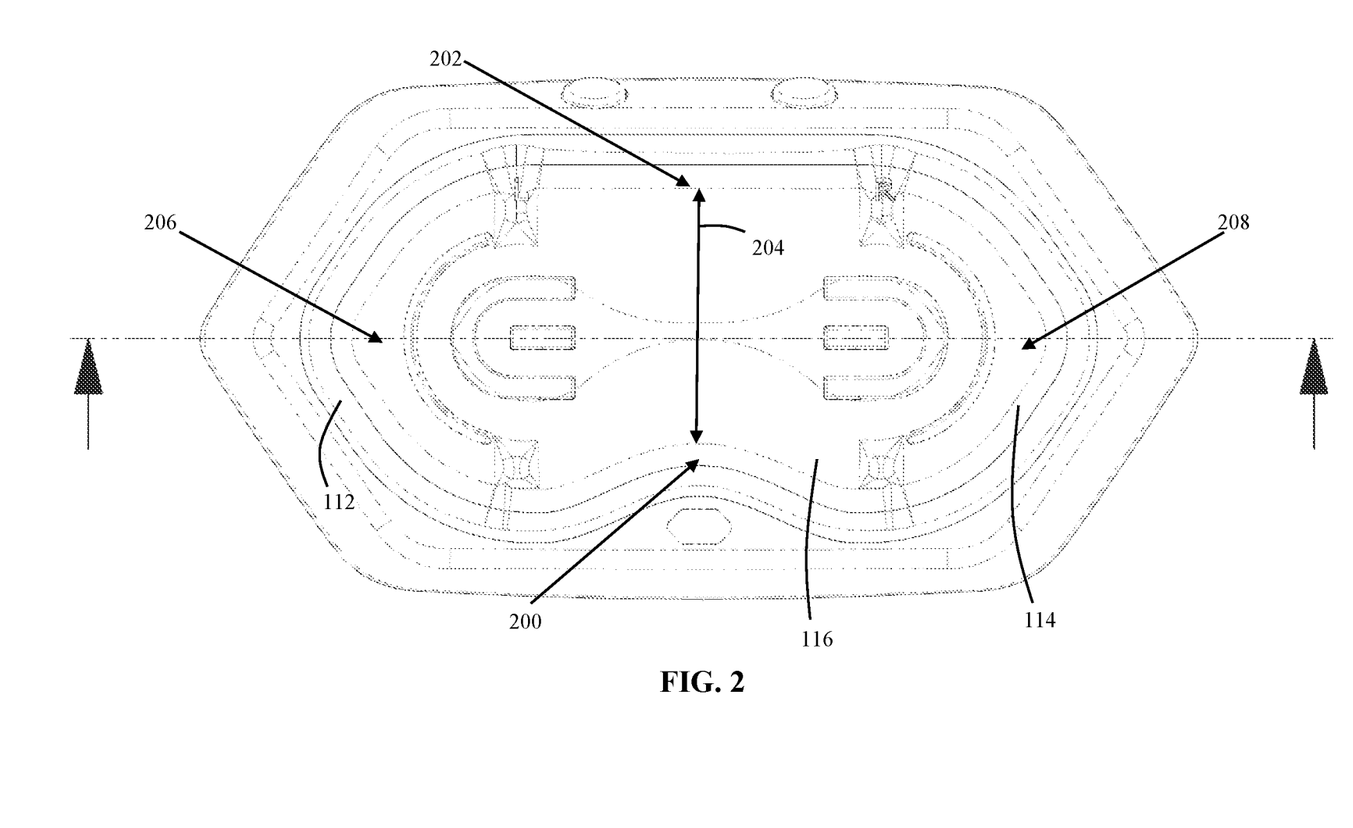
FIG. 2 is top plan view of the vibrating base assembly, in accordance with the present invention.

As best depicted in FIGS. 1-3, the assembly 100 also beneficially includes the upper support wall 112 coupled thereto. The upper support wall 112 is beneficially of a polymeric material, defining at least a portion of the upper surface 104 defining the concave recess 110, with a bottom wall portion 116 defining a portion of the upper surface 104 and defining a lens support plane 310 parallel and non co-planar with a base support plane 312 defined by the bottom surface 700, and with a sidewall portion 114 spanning inwardly toward the housing cavity 300 from the upper edge 108 of the base housing 102 and surrounding the bottom wall portion 116. In one embodiment, the upper support wall 112 is selectively removably coupled to the base housing 102 to facilitate sanitation of the assembly 100, i.e., by removing the upper support wall 112 from the base housing 102 and separately cleaning, washing, and drying it before returning the upper support wall 112 to the assembly 100. In another embodiment, the upper support wall 112 is permanently affixed to the base housing 102 as part of a single monolithic assembly structure, i.e., a single, continuous structure. The upper support wall 112 is of a TPU silicone material in a preferred embodiment of the present invention. The upper support wall 112 is also preferably of a thickness (that may be uniform) of 0.2-0.4 cm.

In accordance with another feature of the present invention, the assembly 100 may also include an internal support member 314 retaining the at least one vibration motor 302, 304, wherein the at least one vibration motor 302, 304 is adjacent and below (and may support) the bottom wall portion 116. As used herein, "adjacent" is defined as directly touching or within 0.5 inches of the bottom wall portion 116. The internal support member 314 is designed to structurally support or protect the at least one vibration motor 302, 304 from damage or injury caused by external forces. The at least one vibration motor 302, 304 is approximately between 2 mm and 6 mm, although it may be slightly larger when encapsulated in the internal support member 314.

Referring now to FIG. 2, the sidewall portion 114 may include at least one arcuate portion 200 defining, with an opposing surface of the sidewall portion 202, a central width 204, and defining two defined circular portions 206, 208 partially defined with the at least one arcuate portion 200 interposed thereon, the two defined circular portions configured to support and/or compressively retain the two contact lens containers 500, 502. Specifically, the first defined circular portion 206 is configured to support the first contact lens container 500 (corresponding to, for example, the left eye contact lens container) and the second defined circular portion 208 is configured to support the second contact lens container 502 (corresponding to, for example, the right eye contact lens container).

In an exemplary embodiment, the assembly 100 comprises two vibration motors 302, 304 with one of the two vibration motors 302, 304 disposed adjacent and below the bottom wall portion 116 of each of the two defined circular portions 206, 208. As used herein, "adjacent" is defined as directly touching or within 0.5 inches of the bottom wall portion 116 of each of the two defined circular portions 206, 208. This placement and configuration beneficially improves the efficiency and effectiveness of the cleaning of the contact lenses. The close proximity between the two vibration motors 302, 304 and the two defined circular portions 206, 208 results in a more effective sanitation and cleaning of the contact lenses housed within the contact lens containers because the frequency of the vibration generated by the two vibration motors 302, 304 is greater closer to the source, i.e., to the two vibration motors 302, 304. As such, the greater frequency near the contact lens containers increases the vibration of the contact lens solution within the contact lens containers and the contact lenses housed therein, resulting in a continued vibration that stimulates the back-and-forth movement of the contact lenses against the contact lens solution. This movement mimics the rubbing of a user's fingertips on contact lenses and the resulting removal of residue from the lenses, but eliminates and prevents the damage that is often caused to the contact lenses by the excessive use of rubbing fingertips. In this way, placement of the two vibration motors 302, 304 adjacent and below the bottom wall portion 116 of each of the two defined circular portions 206, 208 (wherein the two defined circular portions support two contact lens containers 500, 502) significantly contributes to the effectiveness of the cleaning function performed by the assembly 100.

The assembly 100 may also include a first side retention member 118 protruding from the sidewall portion 114 on one of the two defined circular portions 206, 208 and of the friction-inducing, deformable, and polymeric material; and a second side retention member 120 opposing the first side retention member 118 protruding from the sidewall portion 114 on another of the two defined circular portions 206, 208 and of the friction-inducing, deformable, and polymeric material. The two retention members 118, 120 are deformable in that they are capable of being repeatedly manipulated without tearing and are friction-inducing to beneficially aid in the cleaning function of the assembly 100 and to keep and compressively retain the two contact lens containers 500, 502 substantially in a stationary location within the two defined circular portions 206, 208 during use of the assembly 100.

In an exemplary embodiment of the present invention, the side retention members 118, 120 are substantially thin, narrow, discontinuous, and have rounded edges. As used herein, "discontinuous" is defined as not completely surrounding or connecting at a point. As mentioned above, the friction-inducing material may include organic and non-organic substances such as resin, ceramics, fibers, and metals. In an exemplary embodiment, the friction-inducing material is a natural rubber, chloroprene, polysiloxane, nitrile butadiene rubber (NBR), ethylene propylene diene monomer (EPDM), styrene-butadiene rubber (SBR), isobutylene isoprene, fluorosilicone rubber, or another elastomer having a high coefficient of friction with respect to other contact materials (friction coefficient ranging between 1.0 and 4.0). In alternate embodiments, the assembly 100 may comprise only a single side retention member 118.

Similarly, the assembly 100 may also include at least one floor retention member 122 protruding from the bottom wall portion 116 on and centrally disposed on one of the two defined circular portions 206, 208, partially surrounded by the first side retention member 118, and of the friction-inducing, deformable, and polymeric material; and at least one floor retention member 124 protruding from the bottom wall portion 116 on and centrally disposed on another of the two defined circular portions 206, 208, partially surrounded by the second side retention member 120, and of the friction-inducing, deformable, and polymeric material. The floor retention members 122, 124 are operably configured to serve the same functions as the side retention members 118, 120 and, in one embodiment, embody the same dimensions, properties, and characteristics as the side retention members 118, 120. In alternate embodiments, the assembly 100 may comprise only a single floor retention member 122 or may comprise at least one floor retention member 122 in conjunction with at least one side retention member 118.

Figure 6:
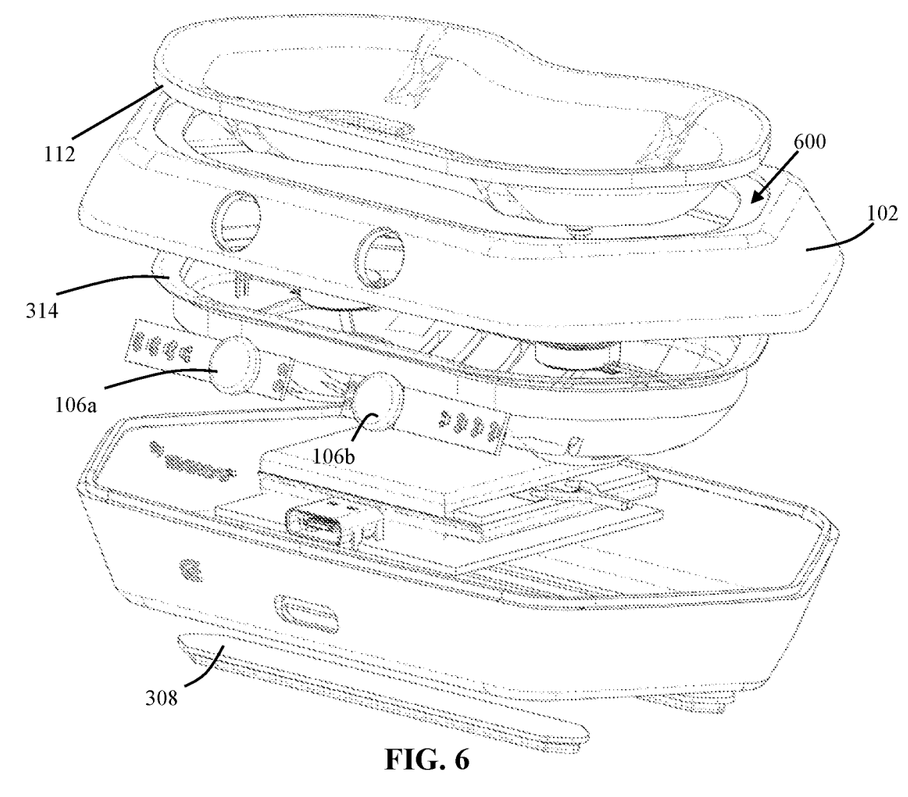
FIG. 6 is an exploded front view of the vibrating base assembly, in accordance with an exemplary embodiment of the present invention.

As seen in FIG. 6, the present invention includes a housing ledge 600 recessed from the upper edge 108 and with the upper support wall 112 selectively removably coupled thereto, the upper support wall 112 of a monolithic structure, wherein "monolithic" is defined as a single, continuous structure. The recessed configuration of the housing ledge 600 beneficially prevents the upper support wall 112 from protruding outwardly away from the assembly 100 in a way that may cause external items to get caught thereon and to accidentally cause the assembly 100 to slip, slide, or fall.

In accordance with a further feature, the assembly 100 includes an electronic controller 316 electrically coupled to the power source 306 and communicatively coupled to the at least one vibration motor 302, 304. The electronic controller 316 may comprise an electronic screen or at least one button which may be selectively manipulated by a user to control the power source 306, e.g., to turn the assembly 100 on or off, and to control the at least one vibration motor 302, 304, e.g., to select the specific operation mode desired by the user. The electronic controller 316 may communicate with the at least one vibration motor 302, 304 over a network 1200 using a short-range communication protocol, for example, a Bluetooth communication protocol, which may also operate as a receiver, transmitter, and/or transceiver. The PAN interface may permit the electronic controller 316 to connect wirelessly to another electronic computing device, e.g., software or mobile application, via a peer-to-peer connection or other communicatively coupled configuration. The network interface(s) may also include a local area network (LAN) interface. The LAN interface may be, for example, an interface to a wireless LAN, such as a Wi-Fi network. In one embodiment, there is a wireless LAN that provides the electronic controller 316 with access to the Internet for receiving and sending inputs/messages to, for example, an administrator server or other electronic device over, for example, the Internet. The range of the LAN interface may generally exceed the range available via the PAN interface. Typically, a connection between two electronic devices via the LAN interface may involve communication through a network router or other intermediary device. Additionally, the network interface(s) may include the capability to connect to a wide area network (WAN) via a WAN interface. The WAN interface may permit a connection to a cellular mobile communications network. The WAN interface may include communications circuitry, such as an antenna coupled to a radio circuit having a transceiver for transmitting and receiving radio signals via the antenna. The radio circuit may be configured to operate in a mobile communications network, including but not limited to global systems for mobile communications (GSM), code division multiple access (CDMA), wideband CDMA (WCDMA), and the like.

The assembly 100 also features two modes of operation, namely, a "sleep" mode and a "fast" mode, which the user may select based on user needs and preferences. Specifically, in accordance with an exemplary embodiment, the assembly 100 comprises at least two switches 106a, 106b translatably coupled to the base housing 102, wherein one of the at least two switches 106a is operably configured to induce the vibration from the at least one vibration motor 302, 304 in a first mode with a constant vibration for a first mode period of time and a first mode vibrational rotations per minute and another of the at least two switches 106b is operably configured to induce the vibration from the at least one vibration motor 302, 304 in a second mode with a cyclic constant vibration for a second mode period of time and a second mode vibrational rotations per minute, wherein the first mode vibrational rotations per minute is less than the second mode vibrational rotations per minute. As used herein, the "sleep" mode corresponds to the first mode and the "fast" mode corresponds to the second mode. The first mode (interchangeably referred to herein as the "sleep" mode) is operably configured to be used once a day, before the user goes to sleep, to allow for cleaning of the contact lenses throughout the night when they are typically not in use. It provides a gentle, overnight, intermittent lens cleaning. The first mode functions on a 12-hour sleep cycle and performs 3 cycles per hour for a combined total of 36 cycles in 12 hours. The vibration motors 302, 304 vibrate at 1,200 RPM for 60 seconds, stop after 60 seconds, and resume again after 20 minutes. Said differently, the vibration motors 302, 304 vibrate for 60 seconds every 20 minutes. In one embodiment, the progress of the two modes of operation is indicated by an audio or visual indicator emanating from the switches 106a, 106b, e.g., by a light or tone. Under the first mode, the indicator light emanating from the switch 106a dims to 50% after the first 60 seconds of running. If the switch 106a is not activated or pressed, the cycle automatically ends after 12 hour cycle and the indicator light dims completely to 0%. If the switch 106a is not activated or pressed during the cycle, the cycle ends and the indicator light dims completely to 0%.

The second mode (interchangeably referred to herein as the "fast" mode) is operably configured to provide a faster cleaning of the contact lenses than the first mode, which is accomplished by the greater vibrational rotations per minute produced under the second mode than under the first mode. This second mode of operation is ideal when contact lenses need to be cleaned in a shorter period of time, but this second mode of operation should preferably be used no more than once a day. The second mode functions on a 3-minute cycle and performs one uninterrupted 3-minute cycle. When the switch 106b is activated or pressed once, the indicator light emanating from the switch 106b turns on at 100% brightness and remains blinking (at 0.5-seconds frequency) during the duration of the 3-minute cycle. The vibration motors 302, 304 vibrate at 1,600 RPM FOR 3 minutes and shut off automatically at the conclusion of the cycle. When the switch 106b is activated or pressed a second time, the assembly 100 is shut off.

Before activating either mode of operation, the contact lenses must be placed within the contact lens containers 500, 502 along with fresh contact lens solution, e.g., cleaning solution, multi-rinse solution, multipurpose solution, etc., and the contact lens containers 500, 502 are then placed within the two defined circular portions 206, 208. Without the contact lens solution, the vibration generated by the at least one vibration motor 302, 304 may cause damage, e.g., tearing, scratching, etc., to the contact lenses rather than effectively clean the contact lenses as is intended. As such, each contact lens must rest within approximately 2.5 mL of contact lens solution. For adequate rubbing and rinsing, approximately 5 mL of solution (2.5 mL/lens) should be used. The average contact lens container 500, 502 holds approximately 2.5 mL of solution, the amount necessary to properly disinfect the contact lens.

Figure 4:
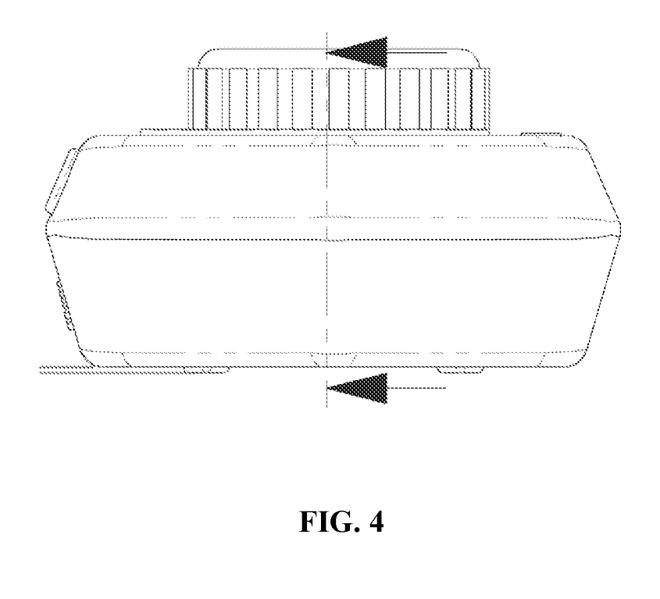
FIG. 4 is an elevational side view of the vibrating base assembly, in accordance with the present invention.

An improvement has also been disclosed that is designed to be used in combination with the pair of contact lens containers 500, 502 having a lens base 504 and a lens cap 506 selectively removably coupled to the lens base 506. The lens base 504 and the lens cap 506 are best seen in FIGS. 4-5. The lens cap 506 is preferably tightened over the lens base 506 during use of the assembly 100 to prevent the contact lenses and contact lens solution from escaping the contact lens containers 500, 502 and to prevent the contact lens solution from evaporating or drying up. The improvement comprises the vibrating base assembly 100 with the base housing 102 defining the housing cavity 300, with the upper edge 108, with the at least one vibration motor 302, 304 disposed within the housing cavity 300, electrically coupled to the power source 306, and operably configured to selectively induce a vibration therefrom with the at least one switch 106 coupled to the base housing 102. The bottom surface 700 and upper surface 104 oppose the bottom surface 700 of the vibrating base assembly 100. The improvement also includes the upper support wall 112 of a friction-inducing, deformable, and polymeric material, defining at least a portion of the upper surface 104, with the bottom wall portion 116, and with the sidewall portion 114 surrounding the bottom wall portion 116 and spanning inwardly toward the housing cavity 300 from the upper edge 108 of the base housing 102 to define the concave recess 110 relative to the upper edge 108 of the base housing 102 and with the lens base 504 of the pair of contact lens containers 500, 502 disposed therein and supported with the upper support wall 112, the upper support wall 112 operably coupled to the at least one vibration motor 302, 304 and to receive a vibration thereon upon activation of the at least one switch 106.

In one embodiment, the bottom wall portion 116 defines a portion of the upper surface 104 and defines the lens support plane 310 parallel and non co-planar with the base support plane 312 defined by the bottom surface 700. The lens support plane 310 is operably configured to provide an adequate support surface for retention of the pair of contact lens containers 500, 502. The base support plane 312 is operably configured to provide a stable bottom surface for the base housing 102 of the assembly 100 to rest on.

The improvement may also include the at least one support pad 308 of a friction-inducing, deformable, and polymeric material and at least partially defining the bottom surface 700 of the vibrating base assembly 100. As explained in greater detail above, the support pad 308 is operably configured to generate friction between the assembly 100 and the surface on which it is laid to rest to beneficially avoid the assembly 100 from inadvertently sliding, slipping, or falling.

In accordance with a further feature, the assembly 100 includes the internal support member 314 retaining the at least one vibration motor 302, 304 to house, shield, and protect the at least one vibration motor 302, 304 from damage caused by external forces.

The sidewall portion 114 may further include the at least one arcuate portion 200 defining, with an opposing surface of the sidewall portion 202, the central width 204, and defining two defined circular portions 206, 208 partially defined with the at least one arcuate portion 200 interposed thereon, the two defined circular portions configured to support the at least one contact lens container 500.

In an alternate embodiment of the present invention, the assembly 100 comprises at least one of the first side retention member 118 protruding from the sidewall portion 114 and of the friction-inducing, deformable, and polymeric material; the second side retention member 120 opposing the first side retention member 118 protruding from the sidewall portion 114 and of the friction-inducing, deformable, and polymeric material; the floor retention member 122 protruding from the bottom wall portion 116 and of the friction-inducing, deformable, and polymeric material; or the floor retention member 124 protruding from the bottom wall portion 116 and of the friction-inducing, deformable, and polymeric material. Said differently, the assembly may include one, some, or all of the first side retention member 118, the second side retention member 120, the floor retention member 122, or the floor retention member 124, all of which perform a similar function, namely, retaining the pair of contact lens containers 500, 502 within the two defined circular portions 206, 208 and maintaining the pair of contact lens containers 500, 502 in a substantially stationary position during use of the assembly 100.

The improvement also includes the electronic controller 316 electrically coupled to the power source 306 and communicatively coupled to the at least one vibration motor 302, 304; and the at least one switch translatably coupled to the base housing 102, wherein the at least one switch is operably configured to induce the vibration from the at least one vibration motor 302, 304 in a first mode with a constant vibration for a first mode period of time and a first mode vibrational rotations per minute. Said differently, the at least one switch may be operably configured to generate a first mode vibrational rotations per minute, a second mode vibrational rotations per minute, or both a first and a second mode vibrational rotations per minute. In a preferred embodiment, the assembly 100 comprises two modes of operation, namely, a first and a second mode, to beneficially provide the user with more personalized vibrational modes of operation designed to address different user needs. In an alternate embodiment, however, the assembly 100 may only comprise a single mode of operation, i.e., a first or a second mode, to address a specific and targeted user need.

The cross-sectional view of FIG. 5 and the exploded view of FIG. 6 best depict the various components of the assembly 100.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A vibrating base assembly for cleaning contact lenses comprising:
a base housing defining a housing cavity, with a bottom surface, with an upper edge, with at least one vibration motor disposed within the housing cavity, electrically coupled to a power source, and operably configured to selectively induce a vibration therefrom with at least one switch coupled to the base housing;
an internal support member disposed within the housing cavity and retaining the at least one vibration motor; and
an upper support wall:
selectively removably coupled to the base housing;
with a bottom wall with a bottom surface and a sidewall surrounding the bottom wall of the upper support wall;
with an upper surface formed with the bottom wall and the sidewall of the upper support wall, opposing the bottom surface of the base housing, spanning inwardly toward the housing cavity from the upper edge of the base housing to define a concave recess relative to the upper edge of the base housing and sized to receive and configured to directly contact two contact lens containers, the at least one vibration motor directly touching and below the bottom surface of the bottom wall and interposed between the internal support member and the bottom wall of the upper support wall; and
made of a friction-inducing, deformable, and polymeric material and configured to directly contact and support the two contact lens containers and operably configured to receive a vibration thereon upon activation of the at least one switch.

2. The vibrating base assembly for cleaning contact lenses according to claim 1, further comprising:
at least one support pad made of a friction-inducing material and at least partially defining the bottom surface of the base housing of the vibrating base assembly.

3. The vibrating base assembly for cleaning contact lenses according to claim 1, further comprising:
the upper support wall made of the polymeric material, with the bottom wall of the upper support wall defining a lens support plane parallel and non co-planar with a base support plane defined by the bottom surface of the base housing, and with the sidewall of the upper support wall spanning inwardly toward the housing cavity from the upper edge of the base housing.

4. The vibrating base assembly for cleaning contact lenses according to claim 3, wherein:
the sidewall of the upper support wall portion includes at least one arcuate portion defining, with an opposing surface of the sidewall of the upper support wall, a central width, and defining two defined circular portions partially defined with the at least one arcuate portion interposed thereon, the two defined circular portions configured to support two contact lens containers.

5. The vibrating base assembly for cleaning contact lenses according to claim 4, further comprising:
two vibration motors with one of the two vibration motors disposed adjacent and below the bottom wall of the upper support wall of each of the two defined circular portions.

6. The vibrating base assembly for cleaning contact lenses according to claim 4, further comprising:
a first side retention member protruding from the sidewall of the upper support wall on one of the two defined circular portions and of the friction-inducing, deformable, and polymeric material; and
a second side retention member opposing the first side retention member protruding from the sidewall of the upper support wall portion on another of the two defined circular portions and of the friction-inducing, deformable, and polymeric material.

7. The vibrating base assembly for cleaning contact lenses according to claim 6, further comprising at least one floor retention member protruding from the bottom wall of the upper support wall on and centrally disposed on one of the two defined circular portions, partially surrounded by the first side retention member, and of the friction-inducing, deformable, and polymeric material; and
at least one floor retention member protruding from the bottom wall of the upper support wall on and centrally disposed on another of the two defined circular portions, partially surrounded by the second side retention member, and of the friction-inducing, deformable, and polymeric material.

8. The vibrating base assembly for cleaning contact lenses according to claim 3, wherein the base housing further comprises:
a housing ledge recessed from the upper edge and with the upper support wall selectively removably coupled thereto, the upper support wall of a monolithic structure.

9. The vibrating base assembly for cleaning contact lenses according to claim 3, further comprising:
an electronic controller electrically coupled to the power source and communicatively coupled to the at least one vibration motor; and
at least two switches translatably coupled to the base housing, wherein one of the at least two switches is operably configured to induce the vibration from the at least one vibration motor in a first mode with a constant vibration for a first mode period of time and a first mode vibrational rotations per minute and another of the at least two switches is operably configured to induce the vibration from the at least one vibration motor in a second mode with a cyclic constant vibration for a second mode period of time and a second mode vibrational rotations per minute, wherein the first mode vibrational rotations per minute is less than the second mode vibrational rotations per minute.

10. In combination with a pair of contact lens containers having a lens base and a lens cap selectively removably coupled to the lens base, the improvement comprising:
a vibrating base assembly with a base housing with a bottom surface, defining a housing cavity, with an upper edge, with at least one vibration motor disposed within the housing cavity, electrically coupled to a power source, and operably configured to selectively induce a vibration therefrom with at least one switch coupled to the base housing;
an internal support member disposed within the housing cavity and retaining the at least one vibration motor; and
an upper support wall selectively removably coupled to the base housing, formed with a bottom wall with a bottom surface and with a sidewall surrounding the bottom wall, with an upper surface formed with the bottom wall and sidewall of the upper support wall and spanning inwardly toward the housing cavity from the upper edge of the base housing to define a concave recess relative to the upper edge of the base housing, configured to directly contact and support the pair of contact lens containers, and made of a friction-inducing, deformable, and polymeric material configured to directly contact the pair of contact lens containers, prevent output of excessive noise, and operably coupled to the at least one vibration motor and receive the vibration thereon upon activation of the at least one switch, wherein the at least one vibration motor is directly touching and below the bottom surface of the bottom wall of the upper support wall and interposed between the internal support member and the bottom wall of the upper support wall.

11. The improvement according to claim 10, wherein:
the bottom wall of the upper support wall defines a lens support plane parallel and non co-planar with a base support plane defined by the bottom surface.

12. The improvement according to claim 10, further comprising:
at least one support pad of a friction-inducing, deformable, and polymeric material and at least partially defining the bottom surface of the vibrating base assembly.

13. The improvement according to claim 10, wherein:
the sidewall of the upper support wall includes at least one arcuate portion defining, with an opposing surface of the sidewall of the upper support wall, a central width, and defining two defined circular portions partially defined with the at least one arcuate portion interposed thereon, the two defined circular portions configured to support at least one contact lens container.

14. The improvement according to claim 10, further comprising at least one of:
a first side retention member protruding from the sidewall of the upper support wall and of the friction-inducing, deformable, and polymeric material;
a second side retention member opposing the first side retention member protruding from the sidewall of the upper support wall and of the friction-inducing, deformable, and polymeric material;
a floor retention member protruding from the bottom wall of the upper support wall and of the friction-inducing, deformable, and polymeric material; or a floor retention member protruding from the bottom wall of the upper support wall and of the friction-inducing, deformable, and polymeric material.

15. The improvement according to claim 10, further comprising:
an electronic controller electrically coupled to the power source and communicatively coupled to the at least one vibration motor; and
at least one switch translatably coupled to the base housing, wherein the at least one switch is operably configured to induce the vibration from the at least one vibration motor in a first mode with a constant vibration for a first mode period of time and a first mode vibrational rotations per minute.

16. The improvement according to claim 15, wherein:
the at least one switch is operably configured to induce the vibration from the at least one vibration motor in a second mode with a cyclic constant vibration for a second mode period of time and a second mode vibrational rotations per minute.

* * * * *